United States Patent [19]

Herold

[11] Patent Number: 4,890,931

[45] Date of Patent: Jan. 2, 1990

[54] MIXER FORK FOR DENTAL CAPSULES

[75] Inventor: Wolf-Dietrich Herold, Seefeld, Fed. Rep. of Germany

[73] Assignee: ESPE Stiftung & Co. Produktions - und Vertriebs KG, Seefeld, Fed. Rep. of Germany

[21] Appl. No.: 192,707

[22] Filed: May 11, 1988

[30] Foreign Application Priority Data

May 14, 1987 [DE] Fed. Rep. of Germany .. 8706965[U]

[51] Int. Cl.$^4$ .................. B01F 11/00; A61C 5/06
[52] U.S. Cl. .................... 366/209; 366/216; 366/602
[58] Field of Search ............. 366/209, 210, 211, 212, 366/213, 214, 215, 216, 219, 602, 110, 111, 112; 269/55, 166, 167, 170, 171, 188, 257, 254 R, 254 CS, 287; 74/60, 86

[56] References Cited

U.S. PATENT DOCUMENTS

| | | | |
|---|---|---|---|
| 416,096 | 11/1889 | Dom | 269/166 |
| 1,413,651 | 4/1922 | Burnett | 366/602 X |
| 1,490,214 | 4/1924 | Johnson | 366/602 X |
| 2,151,123 | 3/1939 | Lavine | 366/211 |
| 2,201,428 | 5/1940 | Chott | 366/602 X |
| 2,597,536 | 5/1952 | Shields | 366/211 |
| 2,759,712 | 8/1956 | Hvistendahl | 366/602 X |
| 3,218,058 | 11/1965 | Smith | 269/166 |
| 3,749,371 | 7/1973 | Folkenroth et al. | 366/209 |
| 4,074,900 | 2/1978 | Drury | 366/602 X |

FOREIGN PATENT DOCUMENTS

| | | | |
|---|---|---|---|
| 2755564 | 6/1978 | Fed. Rep. of Germany | 269/166 |
| 2810678 | 9/1978 | Fed. Rep. of Germany | 366/602 |

*Primary Examiner*—Philip R. Coe
*Assistant Examiner*—Scott J. Haugland
*Attorney, Agent, or Firm*—Foley & Lardner, Schwartz, Jeffery, Schwaab, Mack, Blumenthal & Evans

[57] ABSTRACT

A mixer for dental capsules has a fork-type capsule holder which includes a pair of rigid arms (1, 2) one of which is provided with a pin (10) that passes through an opening (11) provided in the other arm (1). A helical spring (13) disposed about the pin (10) creates a tilting moment about the capsule holding location which causes the pin (10) to be caught by edges forming the opening (11), thereby producing a self-locking action which is not released during the mixing movement. For inserting and removing a capsule (5) in the inoperative condition of the mixer, the fork may be readily opened by pulling a handle (16) provided on the one arm (2) against the relatively weak force of the spring (13).

11 Claims, 1 Drawing Sheet

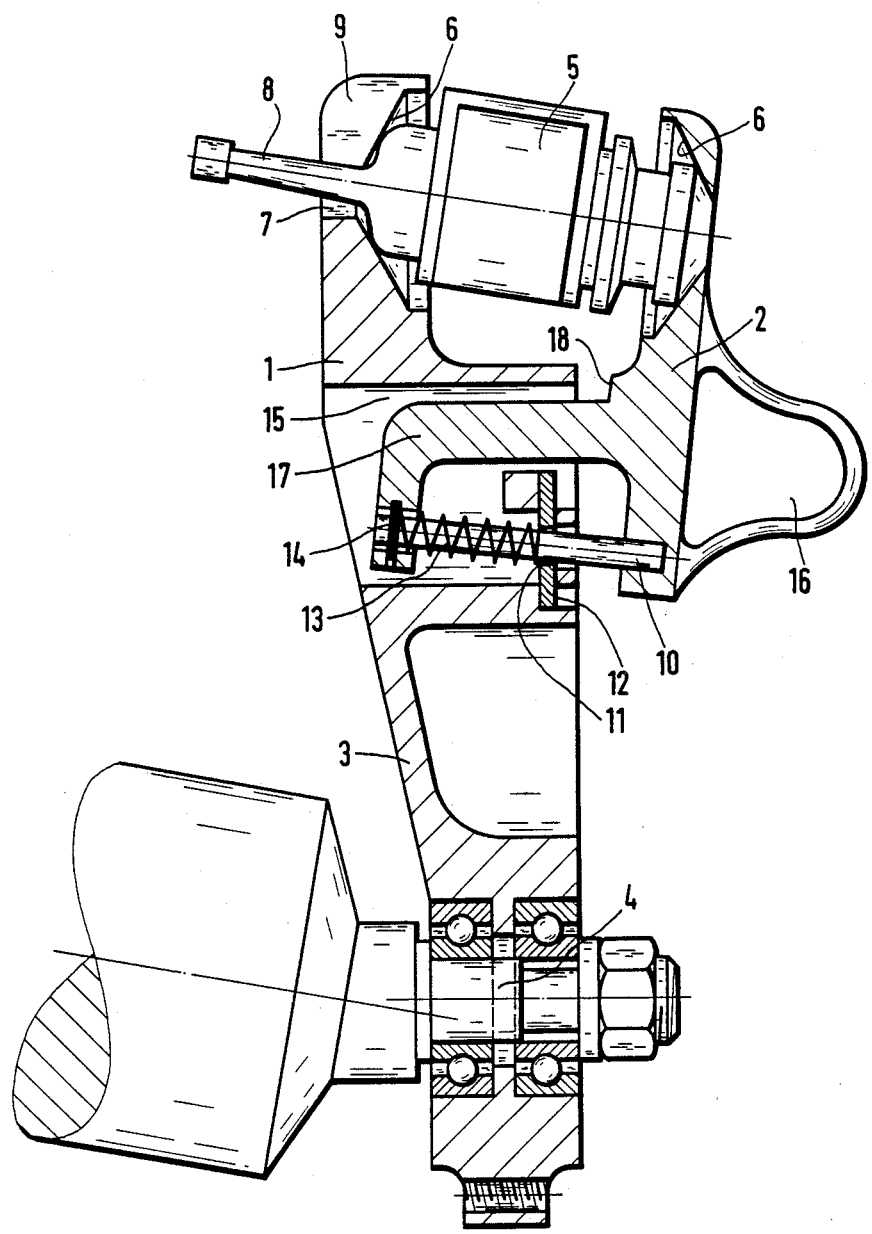

MIXER FORK FOR DENTAL CAPSULES

- Mixing capsules are used in the dental field, in which materials of predetermined amounts - usually one powdery and one liquid component - are thoroughly mixed by means of an electrically driven mixer to produce a ready-to-use cement or filler, such as a synthetic composition or amalgam.

A mixer of this type is known from U.S. Pat. No. 3,749,371, wherein the mixing capsule is clamped between the resilient arms of a retaining fork which is subjected to oscillatory movement. Mass acceleration forces above 100 g (g=gravity) occur during such movement which result in correspondingly high stress on the material of the retaining fork during each reversal of the movement. Further, these mass acceleration forces are superimposed by impulse forces of the material reciprocating within the capsule, which forces may reach particularly high values with the comparatively heavy silver amalgams. Conventional mixer forks are therefore made of high-strength spring steel. Nevertheless, stresses that occur during the mixing operation may cause fracture of the fork. To avoid hazards caused by the capsule being shot off the fork in such a case, modern mixers are provided with a hood covering the oscillating space of the fork.

Commonly available mixing capsules vary in length between about 25 and 35 mm depending on the producer and on the type and amount of substances to be mixed. To ensure safe retaining of the capsule during the mixing process, the arms of the mixing force are required firmly to press against the ends of the capsule. The further requirement that even the shortest capsule must be held safely leads to the fact that the arms of the fork must be widely opened by being bent against the resilient bias to insert a longer capsule. It has been found in practice that very short capsules cannot be retained safely and that very long capsules cause damages of the resilient fork. Also, the resiliency of the retaining fork decreases when longer capsules are frequently inserted so that particularly shorter capsules are held less and less safely.

Due to the use of resilient forks, correspondingly great forces must be excerted to bend the fork arms apart when inserting and removing a capsule. Particularly female assistants do not like this manipulation because bending apart the fork arms by the finger tips may hurt and may cause breaking of the finger nails.

Another problem with conventional mixer forks resides in the fact that the mixing capsule is held between the fork ends substantially exclusively by resilient forces. To ensure a safe hold, the ends of the capsule and the holding portions of the fork arms should be geometrically adapted to each other. However, the geometric relationships vary when the fork arms are spread apart to different extents for receiving capsules of different lengths. Also, different functions of the capsules require correspondingly different shapes of the capsule ends. For instance, in addition to mere mixing capsules, there are also application capsules that have one end closed by a piston and the other end provided with a dispensing nozzle; they are thus shaped different from mere mixing capsules at both retaining positions. It is also for these reasons that the practically exclusively resilient hold between the capsule and the ends of the conventional retaining fork restricts the capability of holding the capsule safely.

It is an object of the present invention to provide a mixer fork which is adapted to retain the capsule safely during the mixing process irrespective of the shape of the capsule, which permits simple handling and easy inserting and removing of a capsule without effort, and which is still of uncomplicated and inexpensive design.

To meet this object, a mixer fork for dental capsules according to the present invention comprises a pair of first and second arms for resiliently holding a capsule, wherein the first arm is provided with a pin extending parallel to the capsule and passing through a hole in the second arm, the pin and hole being so dimensioned that the pin is locked in the opening due to a tilting moment generated by a resilient force acting about the capsule holding location. The resilient force may be small so that the fork arms can be moved apart without effort for inserting and removing a capsule. The resilient force need just be sufficient to cause a tilting between the two fork arms upon engagement of the two ends of a capsule, whereby the pin provided in the one arm locks within the opening provided in the other arm. The capsule is thus retained by a self-locking action. The acceleration forces occurring during the mixing process tend to increase the tilting moment and thus the self-locking effect.

Various measures may be taken to increase the security in holding the capsule. Specifically, the portion of each arm disposed between the capsule holding location and the pin or hole, respectively, may be substantially rigid. Further, the hole may be formed in a disc which is inserted in said second arm and has a greater hardness than the pin, and the hole may be formed with sharp edges. Also, the thickness of the disc may be made substantially smaller than the diameter of the pin.

From the standpoint of assembling the device, it is particularly advantageous to use a helical spring to provide the resilient force and to dispose the spring on the pin between a retainer mounted at the end of the pin and the side of the opening which faces away from the first arm.

In a further preferred embodiment, the pin and the spring are disposed in an opening provided in said second arm. A smooth overall shape of the fork with no projecting parts is thereby achieved.

In another preferred embodiment, in which the second arm has an extension for connecting the fork to a mixer drive, a handle is provided on the first arm at the side remote from the second arm, the handle being adapted to permit an operator to excert a torque counteracting said tilting moment. With this design, the self-locking action is automatically released when the fork is manually opened by pulling the handle.

In a still further embodiment, the two arms are shaped so that, in the absence of a capsule, they engage each other at a location between the pin and the capsule holding location. As a result of this, the two arms of the fork are fixed to each other when no capsule is inserted, thereby preventing excessive stress on the fork when the mixer is operated in this condition.

A positive engagement of the capsule by the fork arms, irrespective of the shape of the capsule ends is advantageously achieved by providing conical recesses in the fork arms.

A preferred embodiment will now be described in detail with reference to the drawing which shows a longitudinal section through a mixer fork with a mixing capsule inserted.

FIG. 1 is a cross-sectional view of a mixer fork according to a preferred embodiment of the present invention.

As shown in the drawing, the fork comprises two arms 1, 2 formed as separate parts. The left arm 1 has a lower extension 3 by which it is mounted via roller bearings on the output shaft of an electrical motor. The bearings are fitted on a portion 4 of the output shaft which is inclined with respect to the axis of rotation, and the arm 1 is held against rotation, such as by springs (not shown), so that rotation of the output shaft is converted into reciprocation of the fork -similar to a swash plate drive - whereby the capsule 5 clamped between the arms 1, 2 is moved to the right and left, according to the drawing.

The upper ends of the arms 1, 2 have their surfaces facing each other provided with conical recesses 6 for receiving the capsule 5. The capsule 5 is thereby positively retained. In at least one of the arms 1, 2 the recess 6 is formed with a central hole 7 for passing a dispensing nozzle 8 as may be provided on application capsules. To facilitate inserting and removing of a capsule 5 having such a dispensing nozzle 8, the upper end of this arm (1) is further provided with a vertical slot 9 which communicates with the hole 7.

As shown in the drawing, a pin 10 is mounted in the arm 2 below the capsule retaining position, which pin extends substantially parallel to the axis of the capsule 5 and passes through a hole 11 provided in a disc 12 inserted in the other arm 1. A helical spring 13 surrounds the pin 10 and bears with its one end against the surface of the disc 12 facing away from the arm 2 and with its other end against a retaining ring 14 by which the end of the pin 10 is mounted on a fork-shaped projection 17 of the arm 2.

The disc 12 is disposed within an opening 15 provided in the arm 1, which opening is so dimensioned that it surrounds the projection 17 of the arm 2 and the pin 10 with the spring 13 also in case no capsule is clamped by the fork. A handle 16 is integrally formed on the outer side of the arm 2 remote from the arm 1 at a position adjacent to the mounting location of the pin 10 and spaced from the capsule holding location. Both arms 1, 2 are rigid molded parts.

In the position shown in the drawing, in which a capsule 5 is inserted between the recesses 6 of the two arms 1, 2, the force of the helical spring 13 produces a tilting moment of the arm 2 about the location where the capsule 5 is held in the recess 6 of the arm 1 or of the arm 2. This tilting moment causes the arm 2 to assume an inclined attitude in which the pin 10, which is fixedly mounted in the arm 2, catches with the opening 11 in the disc 12 as shown in the drawing. In order to increase the locking effect thus produced, the thickness of the disc 12 is substantially smaller than, for instance only one-half of, the diameter of the pin 10, and the opening 11 is formed with sharp edges. In addition, the disc 12 is made of harder material than the pin 10, preferably of hardened steel.

In the tilted position shown in the drawing, the fork cannot be opened by forces acting on the capsule holding locations. During the mixing operation, when the fork is accelerated to the left according to the drawing, the capsule 5 bears on the arm 2 to increase the tilting moment and thereby the self-locking action. When the fork is accelerated to the right, the arm 2 is forced to the left so that, again, the fork is not opened.

For inserting or removing the capsule 5 at stand-still of the mixer, the arm 2 may be moved to the right against the bias of the spring 13 by pulling the handle 16. A torque is thereby created which counteracts the tilting moment caused by the spring 13 about the capsule holding location, and the inclination of the pin 10 relative to the opening 11 is removed so that the pin 10 may now smoothly slide within the slightly larger opening 11. The spring 13 may be relatively weak since it just needs to create the said tilting moment. Thus, by pulling the handle 16, the fork may be readily opened manually without great effort.

When the handle 16 is released, without a capsule having been inserted, the force of the spring 13 will close the fork until a shoulder 18 formed at the inner side of the arm 2 abuts the opposite inner surface of the arm 1. Since the shoulder 18 is laterally offset from the pin 10 in the direction of the capsule holding location, the spring 13 again produces a moment that leads to a tilting of the pin 10 relative to the opening 11 and thus to the self-locking effect described above. As a result, the fork remains safely closed even when the mixer is operated with no capsule inserted; loose parts which may be subjected to unallowable acceleration forces are thus avoided even in this condition.

What is claimed is:

1. A mixer fork for holding a dental capsule during an oscillatory mixing motion of said fork, comprising:
   first and second arms for holding a capsule therebetween, said first and second arms each defining a capsule holding location;
   a pin provided on said first arm and a hole provided in said second arm, said pin passing through said hole and extending substantially parallel to a capsule being held between said capsule holding locations; and
   spring means disposed between said first and second arms for resiliently holding said capsule and for generating a tilting moment between said arms about one of said capsule holding locations, said spring means causing said pin to catch and consequently lock said pin in said hole during the oscillatory mixing motion of said fork.

2. The mixer fork of claim 1 wherein a portion of each arm disposed between the capsule holding location and the pin and, respectively, between the capsule holding location and the hole is substantially rigid.

3. The mixer fork of claim 1, further comprising a disc defining said hole inserted in said second arm and having a greater hardness than said pin, said hole being formed with sharp edges.

4. The mixer fork of claim 3, wherein the thickness of said disc is substantially smaller than the diameter of said pin.

5. A mixer fork for dental capsules, comprising:
   first and second arms for resiliently holding a capsule therebetween;
   said first and second arms each defining a capsule holding location;
   said first arm being provided with a pin extending substantially parallel to the capsule and passing through a hole in said second arm, said pin having a retainer mounted at one end thereof,
   said pin and hole being so dimensioned that the pin is locked in the hole due to a tilting moment, and resilient means for producing said tilting moment about one of said capsule holding locations;

said resilient means comprising a helical spring disposed on said pin between said retainer and the side of said hole nearest said retainer end of the pin.

6. The mixer fork of claim 5, wherein said second arm is formed with an opening, and said pin and spring are disposed within said opening.

7. The mixer fork of claim 1, wherein said second arm has an extension for connecting said fork to a mixer drive, and wherein a handle is provided on a side of said first arm remote from said second arm, said handle being adapted to permit an operator to excert a torque counteracting said tilting moment.

8. The mixer fork of claim 1, wherein said first and second arms are shaped so that they engage each other at a location between said pin and said capsule holding location, when no capsule is inserted in said fork.

9. The mixer fork of claim 1, wherein each arm has a conical recess for retaining a respective capsule end.

10. A mixer fork for dental capsules, comprising:
   first and second arms for resiliently holding a capsule therebetween;
   said first and second arms each defining a capsule holding location;
   said first arm being provided with a pin extending substantially parallel to the capsule and passing through a hole in said second arm;
   said hole having an inner surface;
   resilient means for locking said arms;
   said resilient means causing a tilting moment in said first arm about one of said capsule holding locations;
   said inner surface of the hole thereby bearing against an outer surface of said pin to lock the arms.

11. The mixer fork according to claim 10, wherein said hole and said pin have longitudinal axes which are inclined with respect to each other.

* * * * *